United States Patent [19]

Chibata et al.

[11] Patent Number: 4,519,955

[45] Date of Patent: * May 28, 1985

[54] METHOD FOR OPTICAL RESOLUTION OF DL-α-AMINO ACID OR (±)-α-PHENYLETHANESULFONIC ACID

[75] Inventors: Ichiro Chibata, Suita; Shigeki Yamada, Toyonaka; Chikara Hongo, Osaka; Ryuzo Yoshioka, Kaizuka, all of Japan

[73] Assignee: Tanabe Seiyaku Co., Ltd., Osaka, Japan

[ * ] Notice: The portion of the term of this patent subsequent to Nov. 15, 2000 has been disclaimed.

[21] Appl. No.: 585,767

[22] Filed: Mar. 2, 1984

[30] Foreign Application Priority Data

Mar. 16, 1983 [JP] Japan ................................. 58-43583

[51] Int. Cl.$^3$ ..................... C07C 143/26; C07B 19/00; C07D 207/16; C07D 209/20
[52] U.S. Cl. .......................... 260/501.12; 260/505 P; 548/344; 548/496; 548/498; 548/535; 562/401; 562/442; 562/443; 562/444; 562/445; 562/556; 562/557; 562/559; 562/562; 562/563; 562/565; 562/570

[58] Field of Search ........................ 260/501.12, 505 P; 562/401; 548/496, 498, 535, 344

[56] References Cited

U.S. PATENT DOCUMENTS

| 3,933,902 | 1/1976 | Watanabe et al. | 260/501.12 |
| 3,994,962 | 11/1976 | Shirai et al. | 260/501.12 |
| 4,016,205 | 4/1977 | Kariyone et al. | 260/501.12 |
| 4,115,439 | 9/1978 | Aoki et al. | 260/501.12 |
| 4,233,456 | 11/1980 | Schmand et al. | 260/501.12 |
| 4,309,362 | 1/1982 | Chibata et al. | 260/501.12 |
| 4,415,504 | 11/1983 | Chibata et al. | 260/501.12 |

OTHER PUBLICATIONS

Evans, Journal of the Chemical Society, (London), pp. 1159–1168, (1927).

Primary Examiner—Natalie Trousof
Assistant Examiner—Vera C. Clarke
Attorney, Agent, or Firm—Jordan B. Bierman

[57] ABSTRACT

α-(S)-amino acid.α-phenylethanesulfonate compounds and methods of optical resolution of α-amino acids and α-phenylethanesulfonic acids are described.

35 Claims, No Drawings

METHOD FOR OPTICAL RESOLUTION OF DL-α-AMINO ACID OR (±)-α-PHENYLETHANESULFONIC ACID

This invention relates to a novel method for optical resolution of DL-α-amino acid or (±)-α-phenylethanesulfonic acid. It also relates to a novel diastereoisomeric salt for use in optical resolution of said amino acid or phenylethanesulfonic acid.

It is known that the optical resolution of DL-α-amino acid can be conducted by taking advantage of the difference in solubility of diastereoisomeric salts which are formed by reaction of said racemic modification with an optically active resolving agent. In carrying out said optical resolution of basic or acidic amino acids, an acidic or basic resolving agents are usually used to form the diastereoisomeric salts thereof. On the other hand, the optical resolution of a neutral amino acid may be conducted by the steps of converting the amino acid into a suitable derivative thereof such as N-acyl derivative and then reacting the resultant acidic derivative with a basic resolving agent; or by the steps of converting the amino acid into an ester or amide thereof and then reacting the resultant basic derivative with an acidic resolving agent. Alternatively, if strong acids such as camphorsulfonic acid, bromocamphorsulfonic acid, cholestenonesulfonic acid and hydroxymethanesulfonic acid are used as the resolving agents in these methods, the optical resolution of any amino acids, including neutral amino acids, can be preferably accomplished without converting the amino acid to its derivative because said strong acids react with all of amino acids to form the diastereoisomeric salts thereof. However, such strong acidic resolving agents are still disadvantageous in that they are expensive and/or chemically unstable.

As a result of various investigations, we have now found that (1) α-amino acid can be reacted with α-phenylethanesulfonic acid, which can also exist in the optically active isomeric form, in an aqueous solvent to form the novel salt, i.e., α-amino acid.α-phenylethanesulfonate; and (2) when either one of the reactants to be used in the reaction of α-amino acid and α-phenylethanesulfonic acid is the optically active isomer, one of the resulting two diastereoisomeric salts is always less soluble in a reaction medium and the other is always soluble in the medium. Accordingly, optically active α-phenylethanesulfonic acid can be used as a resolving agent in optical resolution of DL-α-amino acid, and this resolution method of α-amino acid is very useful in the industrial production of optically active α-amino acid. In addition, optically active α-amino acid is a very useful resolving agent in the industrial production of optically active α-phenylethanesulfonic acid.

An object of the present invention is to provide a resolution method of DL-α-amino acid (except DL-p-hydroxyphenylglycine) using optically active α-phenylethanesulfonic acid as a resolving agent. Another object of the present invention is to provide a resolution method of (±)-α-phenylethanesulfonic acid using optically active α-amino acid (except optically active p-hydroxyphenylglycine) as a resolving agent. Other object of the invention is to provide the novel salt, i.e., α-amino acid.α-phenylethanesulfonate (except p-hydroxyphenylglycine.α-phenylethanesulfonate), which is useful for the production of optically active α-amino acid or optically active α-phenylethanesulfonic acid.

According to the present invention, one diastereomer of α-amino acid.α-phenylethanesulfonate (except p-hydroxypheylglycine.α-phenylethanesulfonate) can be prepared by either reacting DL-α-amino acid (except p-hydroxyphenylglycine) with optically active α-phenylethanesulfonic acid or reacting (±)-α-phenylethanesulfonic acid with optically active α-amino acid (except p-hydroxyphenylglycine) in an aqueous solvent to form two diastereoisomeric salts of DL-α-amino acid.optically active α-phenylethanesulfonate or optically active α-amino acid.(±)-α-phenylethanesulfonate, and then isolating a less soluble diastereoisomeric salt therefrom by the difference in solubility of the diastereoisomeric salts.

This reaction can be utilized in the resolution of α-amino acid (except p-hydroxyphenylglycine) or α-phenylethanesulfonic acid. That is, DL-α-amino acid (except p-hydroxyphenylglycine) or (±)-α-phenylethanesulfonic acid can be resolved by using optically active α-phenylethanesulfonic acid or optically active α-amino acid (except p-hydroxyphenylglycine) as a resolving agent in the above reaction, separating the resultant less soluble diastereoisomeric salt, and converting it into the desired optically active α-amino acid or optically active α-phenylethanesulfonic acid.

Examples of the diastereoisomeric salts of the present invention include the salts of (+) or (−)-α-phenylethanesulfonic acid with optically active α-amino acids such as alanine, arginine, valine, leucine, isoleucine, phenylalanine, phenylglycine, tyrosine, tryptophan, serine, threonine, proline, cysteine, glutamic acid, aspartic acid, histidine, ornithine, lysine and citrulline. Preferred examples of said diastereoisomeric salts include the salts of (+) or (−)-α-phenylethanesulfonic acid with optically active valine, arginine, lysine, phenylglycine or leucine. More preferred examples of the salts include the salt of (−)-α-phenylethanesulfonic acid with L-valine, L-arginine, L-lysine, L-phenylglycine or D-leucine, and the salt of (+)-α-phenylethanesulfonic acid with D-valine, D-arginine, D-lysine, D-phenylglycine or L-leucine.

The DL-α-amino acid or (±)-α-phenylethanesulfonic acid to be used in the present invention may be a mixture of equal amounts of D- and L-isomer or (+)- and (−)-isomer, i.e., a racemic mixture, or a mixture composed of a larger amount of one isomer and a smaller amount of the other isomer, i.e., a so-called low-purity optically active isomer. For example, the DL-α-amino acid or (±)-α-phenylethanesulfonic acid may be that obtained by synthesis or a low-purity optically active isomer such as that remaining in the mother liquor after resolution of DL-α-amino acid or (±)-α-phenylethanesulfonic acid according to a conventional method. The optically active isomer or racemic modification of α-amino acid to be used in the present invention may be either in the free form or a salt thereof. Examples of such salt include an inorganic addition salt such as hydrochloride or sulfate, an organic addition salt such as oxalate, benzenesulfonate, toluenesulfonate, xylenesulfonate, chlorobenzenesulfonate, nitrobenzenesulfonate, naphthalenesulfonate or methanesulfonate, and the like. Likewise, optically active or racemic α-phenylethanesulfonic acid to be used in the present invention may be in the free acid form or it may be a salt with an alkali metal such as sodium or potassium, an alkaline earth metal such as calcium or magnesium, ammonia or amine.

The above-mentioned reaction of DL-α-amino acid and optically active α-phenylethanesulfonic acid or the reaction of (±)-α-phenylethanesulfonic acid and optically active α-amino acid can be readily accomplished in a solvent. Any solvents which dissolve said two reactants and do not interfere the salt formation thereof can be used for the purpose of the present invention. Exampls such solvent include water; lower alkanol such as methanol, ethanol, n-propanol or n-butanol; lower alkanone such as acetone; lower alkanoic acid such as acetic acid or propionic acid; or a mixture thereof. It is preferred to carry out the reaction at a temperature of 5° to 80° C. It is also preferred to use 0.3 to 1.5 moles, especially 0.5 to 1.0 moles of the resolving agent (i,e., optically active α-phenylethanesulfonic acid or optically active α-amino acid) per mole of the racemic modification of α-amino acid or α-phenylethanesulfonic acid.

In the above-mentioned reaction, when the racemic modification of valine, arginine, lysine or phenylglycine is used as the DL-α-amino acid and (−)-α-phenylethanesulfonic acid is used as the resolving agent, L-amino acid.(−)-α-phenylethanesulfonate is formed as the less soluble diastereoisomeric salt, and D-amino acid.(−)-α-phenylethanesulfonate is formed as the more soluble diastereoisomeric salt. On the other hand, when the racemic modification of valine, arginine, lysine or phenylglycine is used as the DL-α-amino acid and (+)-α-phenylethanesulfonic acid is used as the resolving agent, D-amino acid.(+)-α-phenylethanesulfonate is formed as the less soluble diastereoisomeric salt and L-amino acid.(+)-α-phenylethanesulfonate is formed as the more soluble diastereoisomeric salt. Further, when the racemic modification of leucine is used as the DL-α-amino acid and optically active α-phenylethanesulfonic acid is used as the resolving agent, L-leucine.(+)-α-phenylethanesulfonate or D-leucine.(−)-α-phenylethanesulfonate is formed as the less soluble diastereoisomeric salt and D-leucine.(+)-α-phenylethanesulfonate or L-leucine.(−)-α-phenylethanesulfonate is formed as the more soluble diastereoisomeric salt.

Likewise, the diastereoisomeric salts of (+) or (−)-α-phenylethanesulfonic acid can be readily formed by reacting the racemic modification thereof with optically active α-amino acid. For example, when (±)-α-phenylethanesulfonic acid is reacted with L-valine, L-arginine, L-lysine or L-phenylglycine, siad L-amino acid.(−)-α-phenylethanesulfonate is formed as the less soluble diastereoisomeric salt and L-amino acid.(+)-α-phenylethanesulfonate is formed as the more soluble diastereoisomeric salt. On the other hand, when (±)-α-phenylethanesulfonic acid is reacted with D-valine, D-arginine, D-lysine or D-phenylglycine, said D-amino acid.(+)-α-phenylethanesulfonate is formed as the less soluble diastereoisomeric salt and D-amino acid.(−)-α-phenylethanesulfonate is formed as the more soluble diastereoisomeric salt. Further, when (±)-α-phenylethanesulfonic acid is reacted with optically active leucine, L-leucine.(+)-α-phenylethanesulfonate or D-leucine.(−)-α-phenylethanesulfonate is formed as the less soluble diastereoisomeric salt and D-leucine.(+)-α-phenylethanesulfonate or L-leucine.(−)-α-phenylethanesulfonate is formed as the more soluble diastereoisomeric salt.

When the diastereoisomeric salts of the amino acid.α-phenylethanesulfonate are formed in the above-mentioned reaction, said diastereoisomeric salts can be readily separated from each other by their difference in solubility. For example, the crystallization of the less soluble diastereoisomeric salt can be carried out by cooling or concentration of the reaction mixture or by adding an organic solvent thereto, and said less soluble salt is thereby obtained as the crystals in high purity. The separated less soluble diastereoisomeric salt is recovered from the reaction mixture according to a conventional solid-liquid separation technique such as filtration and centrifugation. The less soluble diastereoisomeric salt thus obtained may be, if necessary, subjected to a further treatment such as washing or recrystallization.

Each diastereoisomeric salt formed in the above reaction is the novel optically pure salt composed of 1 mole of optically active α-amino acid and 1 mole of optically active α-phenylethanesulfonic acid.

The less soluble diastereoisomeric salt thus obtained can readily be converted to optically active α-amino acid and optically active α-phenylethanesulfonic acid by treating it with an ion-exchange resin or an alkali agent. For example, when an aqueous solution of one diastereoisomeric salt of α-amino acid.α-phenylethanesulfonate is treated with a strong acidic ion-exchange resin, the optically active α-amino acid is adsorbed on the ion-exchange resin and the optically active α-phenylethanesulfonic acid is eluted into the effluent. Moreover, optically active α-amino acid adsorbed on said ion-exchange resin is readily eluted from said resin by a conventional manner such as by treatment with aqueous ammonia. Further, optically active α-phenylethanesulfonic acid thus recovered can used again as the resolving agent of the present invention.

As mentioned hereinbefore, according to the present invention, the desired optically active α-amino acid can be selectively crystallized out in the form of the less soluble diastereoisomeric salt by using (+) or (−)-α-phenylethanesulfonic acid as the resolving agent. Likewise, the desired optically active α-phenylethanesulfonic acid can be selectively crystallized out in the form of the less soluble diastereoisomeric salt by using D or L-α-amino acid as the resolving agent. Since the optically active α-phenylethanesulfonic acid which is used in the present invention is a strong acidic resolving agent, even neutral and acidic amino acids can be directly resolved into each enantiomers thereof without converting them into another derivatives such as an ester or amide derivative thereof. For example, the optical resolution method of the invention can be applied to a variety of acidic, basic and neutral α-amino acids such as alanine, arginine, valine, leucine, isoleucine, phenylalanine, phenylglycine, tyrosine, tryptophan, serine, threonine, proline, cysteine, glutamic acid, aspartic acid, histidine, ornithine, lysine and citrulline, especially an amino acid selected from the group consisting of valine, leucine, arginine, lysine and phenylglycine. Moreover, since optically active α-phenylethanesulfonic acid is a synthetic resolving agent and not the one derived from a naturally occuring substance, either one of (+) and (−)-α-phenylethanesulfonic acid are freely available for the optical resolution of the invention. Other advantage of optically active α-phenylethanesulfonic acid is that it is so stable that it does not undergo racemization under usual conditions of the optical resolution procedures and can be used repeatedly as the resolving agent of the invention.

As is apparent from these facts, therefore, the method of the present invention using the optically active α- phenylethanesulfonic acid is quite useful and advantageous for industrial scale production of optically active α-amino acid.

In addition, although optically active α-phenylethanesulfonic acid which is an excellent resolving agent has hitherto been hardly commercially available even as a chemical reagent (cf. J. Chem. Soc., 1159 (1927)), according to the present invention it can be readily produced on large scale and therefore it enables to supply optically active α-phenylethanesulfonic acid in an industrial scale.

Practical and presently-preferred embodiments of the present invention are illustratively shown in the following Examples. Throughout the specification and claims, the term "lower alkanol" should be interpreted as referring to alkanol having one to four carbon atoms and the term "lower alkanone" and "lower alkanoic acid" should be interpreted as referring to alkanone and alkanoic acid having two to five carbon atoms.

[Optical resolution of DL-α-amino acid]

EXAMPLE 1

A mixture of 10 g of DL-α-amino acid and optically active α-phenylethanesulfonic acid (resolving agent) is dissolved in a solvent under heating. The solution is allowed to stand at room temperature for one day. The resultant precipitates are collected by filtration, washed with a solvent and then dried. The less soluble diastereoisomeric salt of said amino acid thus recovered is dissolved in water (an about 5% aqueous solution of the diastereoisomeric salt is thereby prepared). The solution is passed through a column packed with a strong acidic ion-exchange resin, and the column is washed with water. Then, the column is eluted with 1N aqueous ammonia to liberate the amino acid adsorbed thereon. After the eluate is concentrated to dryness under reduced pressure, about 5 ml of water or methanol are added to the residue. The mixture is cooled, and the resultant precipitates are collected by filtration to given an optically active amino acid. (the optically active amino acid is recovered from the less soluble diastereoisomeric salt in an yield of 85–95%) The yield of the less soluble diastereoisomeric salt and the purity of the optically active amino acid recovered in the above-mentioned experiment are shown in the following Table 1.

EXAMPLE 2

30 g of DL-arginine, 32.1 g of (−)-α-phenylethanesulfonic acid, 38 ml of water and 380 ml of methanol are treated in the same manner as described in Example 1, whereby 13 g of L-arginine.(−)-α-phenylethanesulfonate are obtained as the less soluble diastereoisomeric salt. Then, said diastereoisomeric salt is further treated in the same manner as described in Example 1, whereby 7.3 of L-arginine monohydrochloride are obtained.

$[\alpha]_D^{25}+15.8°$ (C=8, 6N hydrochloric acid) Optical purity: 70% Optical resolution of (±)-α-phenylethanesulfonic acid.

EXAMPLE 3

To 100 ml of water containing 20 g (ca. 0.11 mole) of (±)-α-phenylethanesulfonic acid, an optically active amino acid (0.11 mole) (resolving agent) is added. The mixture is concentrated to dryness under reduced pressure. The residue is dissolved in water or n-butanol (the amount of water or n-butanol is shown in Table 2) under heating. The solution is cooled or methanol (the amount of methanol is shown in Table 2) is added thereto, and the resultant precipitates are collected by filtration and dried. The less soluble diastereoisomeric salt thus recovered is dissolved in water to prepare an aqueous solution, about 10%, thereof. The solution is passed through a column packed with a strong ion-exchange resin. The effluent is concentrated under reduced pressure until an about 50% aqueous solution of optically active α-phenylethanesulfonic acid is obtained. The yield of the less soluble diastereoisomeric salt recovered and the purity of optical active α-phenylethanesulfonic acid are shown in the following Table 2 (the optically active α-phenylethanesulfonic acid is recovered from the less soluble diastereoisomeric salt in an yield of 98–100%).

TABLE 2

| Resolving agents used (optically active α-amino acid | Solvents used (ml) | Yield** (g) | α-phenylethane-sulfonic acid recovered | |
|---|---|---|---|---|
| | | | $[\alpha]_D^{25}$ (C = 1, water) | optical purity*** (%) |
| L-leucine | water (33) | 12 | +4.7° | 76 |
| L-valine | water (75) | 5 | −5.8° | 94 |
| L-arginine | water/methanol (38/380) | 3 | −5.0° | 81 |
| L-lysine | water/methanol (10/190) | 18 | −5.8° | 94 |
| D-phenyl-glycine | n-butanol (450) | 17 | +5.6° | 90 |

*The yield of the less soluble diastereoisomeric salt.

TABLE 1

| DL-α-amino acids used | Resolving agent (g) | Solvents used (ml) | Yield* (g) | Optically active α-amino acids recovered | | | |
|---|---|---|---|---|---|---|---|
| | | | | obtained isomers | $[\alpha]_D^{25}$ | | Optical purity (%) |
| DL-leucine | (+)-isomer (14.2) | water (25) | 7.3 | L-isomer | +9.1° (C = 4, 6N—HCl) | | 60 |
| DL-valine | (−)-isomer (15.9) | water (22) | 2.6 | L-isomer | +24.3° (C = 8, 6N—HCl) | | 87 |
| DL-lysine | (−)-isomer (12.7) | water/methanol (7/120) | 12.0 | L-isomer** | +19.8° (C = 8, 6N—HCl) | | 94 |
| DL-phenyl-glycine | (+)-isomer (12.3) | n-butanol (400) | 9.6 | D-isomer | −150.1° (C = 1, N—HCl) | | 95 |

*The yield of the less soluble diastereoisomeric salt.
**The amino acid obtained is lysine monohydrochloride.

***Optical rotation of optically pure α-phenylethane-sulfonic acid: $[\alpha]_D^{25} + 6.2°$ or −6.2°

What we claim is:

1. A compound comprising an α.(S)-amino acid and α-phenylethanesulfonic acid which is α-amino acid.α-phenylethanesulfonate, exclusive of p-hydroxyphenylglycine.α-phenylethanesulfonate.

2. The compound of claim 1, wherein said α-amino acid and α-phenylethanesulfonic acid are optically active isomers.

3. The compound claimed in claim 1, in which the α-amino acid is selected from the group consisting of alanine, arginine, valine, leucine, isoleucine, phenylalanine, phenylglycine, tyrosine, trytophan, serine, threonine, proline, cysteine, glutamic acid, aspartic acid, histidine, ornithine, lysine and citrulline.

4. The compound claimed in claim 1, in which the α-amino acid is an optically active α-amino acid selected from the group consisting of arginine, valine, leucine, phenylglycine and lysine.

5. The compound claimed in claim 4, which is L-leucine.(+)-α-phenylethanesulfonate, L-valine.(−)-α-phenylethanesulfonate, L-arginine.(−)-α-phenylethanesulfonate, L-lysine.(−)-α-phenylethanesulfonate or D-phenylglycine.(+)-α-phenylethanesulfonate.

6. A method for resolving DL-α-amino acid, exclusive of DL-p-hydroxyphenylglycine comprising
    a. reacting said DL-α-amino acid with optically active α-phenylethanesulfonic acid to yield the diastereoisomeric salt of DL-α-amino acid.optically active α-phenylethanesulfonate,
    b. collecting the less soluble diastereoisomeric salt, and
    c. converting said collected salt into optically active α-amino acid.

7. The method according to claim 6, wherein the DL-α-amino acid is selected from the group consisting of alanine, arginine, valine, leucine, isoleucine, phenylalanine, phenylglycine, tryptophan, tyrosine, serine, threonine, proline, cysteine, glutamic acid, aspartic acid, histidine, ornithine, lysine and citrulline.

8. The method according to claim 6, wherein the DL-α-amino acid is selected from the group consisting of arginine, valine, leucine, phenylglycine and lysine.

9. The method according to claim 6, wherein the optically active α-phenylethanesulfonic acid is used in an amount of 0.3 to 1.5 mole per mole of the DL-α-amino acid.

10. The method according to claim 9, wherein the optically active α-phenylethanesulfonic acid is used in an amount of 0.5 to 1.0 mole per mole of the DL-α-amino acid.

11. The method according to claim 9, wherein said reacting step is carried out in an aqueous solvent.

12. The method according to claim 7, wherein the optically active α-phenylethanesulfonic acid is used in an amount of 0.3 to 1.5 mole per mole of the DL-α-amino acid.

13. The method according to claim 8, wherein the optically active α-phenylethanesulfonic acid is used in an amount of 0.3 to 1.5 mole per mole of the DL-α-amino acid.

14. The method according to claim 12, wherein the optically active α-phenylethanesulfonic acid is used in an amount of 0.5 to 1.0 mole per mole of the DL-α-amino acid.

15. The method according to claim 13, wherein the optically active α-phenylethanesulfonic acid is used in an amount of 0.5 to 1.0 mole per mole of the DL-α-amino acid.

16. The method according to claim 12, wherein said reacting step is carried out in an aqueous solvent.

17. The method according to claim 13, wherein said reacting step is carried out in an aqueous solvent.

18. A method of resolving (±)-α-phenylethanesulfonic acid comprising
    a. reacting said (±)-α-phenylethanesulfonic acid with an optically active α-amino acid, exclusive of optically active p-hydroxyphenylglycine, to form to diastereoisomeric salts of α-amino acid.(±)-α-phenylethanesulfonate,
    b. collecting the less soluble diastereoisomeric salt therefrom, and
    c. converting said collected salt into optically active α-phenylethanesulfonic acid.

19. The method according to claim 18, wherein the optically active α-amino acid is selected from the group consisting of alanine, arginine, valine, leucine, isoleucine, phenylalanine, phenylglycine, tryptophan, tyrosine, serine, threonine, proline, cysteine, glutamic acid, aspartic acid, histidine, ornithine, lysine and citrulline.

20. The method according to claim 19, wherein the optically active α-amino acid is used in an amount of 0.3 to 1.5 mole per mole (±)-α-phenylethanesulfonic acid.

21. The method according to claim 18, wherein the optically active α-amino acid is selected from the group consisting of arginine, valine, leucine, phenylglycine and lysine.

22. The method according to claim 21, wherein the optically active α-amino acid is used in an amount of 0.3 to 1.5 mole of (±)-α-phenylethanesulfonic acid.

23. The method according to claim 18, wherein the optically active α-amino acid is used in an amount of 0.3 to 1.5 mole per mole of (±)-α-phenylethanesulfonic acid.

24. The method according to claim 23, wherein the optically active α-amino acid is used in an amount of 0.5 to 1.0 mole per mole of the (±)-α-phenylethanesulfonic acid.

25. The method according to claim 23, wherein said reacting step is carried out in an aqueous solvent.

26. The method according to claim 20, wherein the optically active α-amino acid is used in an amount of 0.5 to 1.0 mole per mole of the (±)-α-phenylethanesulfonic acid.

27. The method according to claim 22, wherein the optically active α-amino acid is used in an amount of 0.5 to 1.0 mole per mole of the (±)-α-phenylethanesulfonic acid.

28. The method according to claim 20, wherein said reacting step is carried out in an aqueous solvent.

29. The method according to claim 22, wherein said reacting step is carried out in an aqueous solvent.

30. The method of claim 9 wherein said reacting step is carried out in a solvent selected from lower alkanol, lower alkanone, lower alkanoic acid and mixtures thereof.

31. The method of claim 33 wherein said reacting step is carried out in a solvent selected from lower alkanol, lower alkanone, lower alkanoic acid and mixtures thereof.

32. The method of claim 12 wherein said reacting step is carried out in a solvent selected from lower alkanol, lower alkanone, lower alkanoic acid and mixtures thereof.

33. The method of claim 13 wherein said reacting step is carried out in a solvent selected from lower alkanol, lower alkanone, lower alkanoic acid and mixtures thereof.

34. The method of claim 20 wherein said reacting step is carried out in a solvent selected from lower alkanol, lower alkanone, lower alkanoic acid and mixtures thereof.

35. The method of claim 22 wherein said reacting step is carried out in a solvent selected from lower alkanol, lower alkanone, lower alkanoic acid and mixtures thereof.

* * * * *